United States Patent [19]

Huignard et al.

[11] 4,284,324
[45] Aug. 18, 1981

[54] ACOUSTO-OPTICAL IMAGERY SYSTEM BASED ON COHERENT HOLOGRAPHIC DETECTION IN REAL TIME

[75] Inventors: Jean-Pierre Huignard; Jean-Pierre Herriau, both of Paris, France

[73] Assignee: Thomson-CSF, Paris, France

[21] Appl. No.: 917,334

[22] Filed: Jun. 20, 1978

[30] Foreign Application Priority Data

Jun. 24, 1977 [FR] France ............................ 77 19492

[51] Int. Cl.³ ............................................. G03H 1/02
[52] U.S. Cl. ..................................... 350/3.64; 73/603;
350/3.83; 350/3.85; 365/125; 367/8
[58] Field of Search ..................... 350/3.64, 3.69, 3.83,
350/3.84, 3.85, 3.86; 340/5 H; 365/125; 73/603,
605; 367/8, 9, 10

[56] References Cited

U.S. PATENT DOCUMENTS

| | | | |
|---|---|---|---|
| 3,633,407 | 1/1972 | Whitman | 340/5 H X |
| 3,745,812 | 7/1973 | Korpel | 340/5 H X |
| 3,879,989 | 4/1975 | Brenden | 350/3.69 X |
| 3,886,488 | 5/1975 | Bossaert et al. | 340/5 H X |
| 4,138,189 | 2/1979 | Huignard et al. | 350/3.64 |

OTHER PUBLICATIONS

Collins et al., "Pulse Compression by Bragg Diffraction of Light...", *Appl. Phys. Ltrs.*, vol. 11, No. 7, Oct. 1967, pp. 240–242.

Micheron et al., "High Photosensitivity Volume Hologram Recording...", *Optics Commun.*, vol. 18, No. 2, Jul. 1976, pp. 216–217.

Primary Examiner—John K. Corbin
Assistant Examiner—John D. Lee
Attorney, Agent, or Firm—Cushman, Darby & Cushman

[57] ABSTRACT

The invention relates to the acousto-optical imagery of objects transmitting ultrasonic waves; an optical image diffracted by the action of an ultrasonic wave is detected by coherent detection in an electro-optical and photoconductive holographic recording material under an applied field by holographic recording of the interferences between the diffracted order to be imaged formed by the optical wave of pulsation $\omega_o + \omega_s$ (or $\omega_o - \omega_s$) and an optical reference wave having the same pulsations. Imagery is effected in real time by restoration of the object wave by a reading wave having the same pulsation as the reference wave.

5 Claims, 3 Drawing Figures

ACOUSTO-OPTICAL IMAGERY SYSTEM BASED ON COHERENT HOLOGRAPHIC DETECTION IN REAL TIME

This invention relates to acousto-optical imagery systems. The phenomenon of the diffraction of light by ultrasounds has already been used for converting an acoustic transparency into a luminous image. Acousto-optical imagery systems of this type are used in particular for the non-destructive testing of metallic components, for testing the emission of ultrasonic transducers by display of the emissive face or for examining human tissues for example in biomedical applications.

In conventional systems, the imagery bank consists of an optical radiation source (laser), an optical device for forming a convergent cylindrical wave, an ultrasonic wave emitter and an ultrasonic cell in which the object to be analysed is placed, the interaction space between the optical wave and the acoustic wave being located in this cell. The diffracted optical beam then passes through a spatial filter which enables one of the two diffraction images of the first order to be isolated. This image, which is corrected by means of an anamorphic assembly, is then projected on a vidicon tube and may therefore be viewed in real time. An arrangement such as this is attended by several disadvantages. In particular, the image is disturbed by a considerable noise level partly corresponding to that which remains from the redundant diffraction orders because it is not possible to completely filter a single diffracted image with a spatial filter. In addition, the device by which the aberrations are at least partly compensated is expensive. Finally, the display unit only enables a two-dimensional image to be obtained. Stigmatism is only present in the plane perpendicular to the source line while ombroscopy is only present in the perpendicular direction.

According to the invention, there is provided an accousto-optical imagery system based on coherent holographic detection comprising an optical source of pulsation $\omega_o$, a device forming a convergent cylindrical optical wave of pulsation $\omega_o$ from the wave emitted by the source, an ultrasonic cell containing a refractive fluid in which an object to be analysed is placed, an ultrasonic wave emitter emitting an ultrasonic wave of pulsation $\omega_s$, said ultrasonic wave passing through the object to be analysed, said ultrasonic wave and said cylindrical optical wave interacting in the cell to form, by BRAGG diffraction of the optical wave, diffracted orders containing the optical images of said object to be analysed, an additional optical device intended to supply a plane optical reference wave of pulsation $\omega_o + K \omega_s$, k being equal to $+1$ or $-1$, according to whether the diffracted order to be imaged is the order $+1$ or $-1$, said diffracted order and said plane optical reference wave being directed towards said crystal to form interference fringes in said crystal, an electro-optical and photoconductive holographic recording crystal, electrodes to be connected to a voltage source being placed on said crystal, a unit for viewing an image of said object in real time comprising a source to emit a plane optical reading wave having the same pulsation and direction as the reference wave, but being propagated in the opposite direction thereto, and an optical device forming said image of the object in a viewing plane from the beam restored by said crystal, the object thus being viewed in real time.

For a better understanding of the present invention and to show how the same may be carried into effect reference will be made to the following description and the attached drawings among which:

The propagation of an ultrasonic wave in a medium results in a modification to the voluminal mass of the medium and hence to the conditions of propagation of an electromagnetic wave (coherent light). When the interaction medium is water, the immersed ultrasonic emitter produces compression waves. The resulting variations in pressure induce variations $\Delta n$ in the refractive index. The phase network thus formed behaves like a diffraction grating. The phase and amplitude of an incident optical wave are affected by the stratification of the index n of the medium and the optical wave emerging from the interaction zone partly decomposes into diffracted waves.

If $\phi_B$ is the Bragg angle in the diffraction medium, the angular difference between the direction of the energy maximum of the diffracted order and the corresponding direction of the non-diffracted order is $2\phi_B$ with $\sin \phi_B = [(\lambda m)/(2\lambda_s)]$ where $\lambda_m$ is the wave-length of the incident optical wave in the interaction medium and $\lambda_s$ is the wave-length of the sound wave in the same medium. The interaction between an incident optical ray and the corresponding ultrasonic ray takes place when the angle between the two corresponding directions is equal to $(\pi/2) \pm \phi_B$. For example, for an ultrasonic cell containing water, $\phi_B = 2.38 \times 10^{-3}$ radian.

Figure 1:
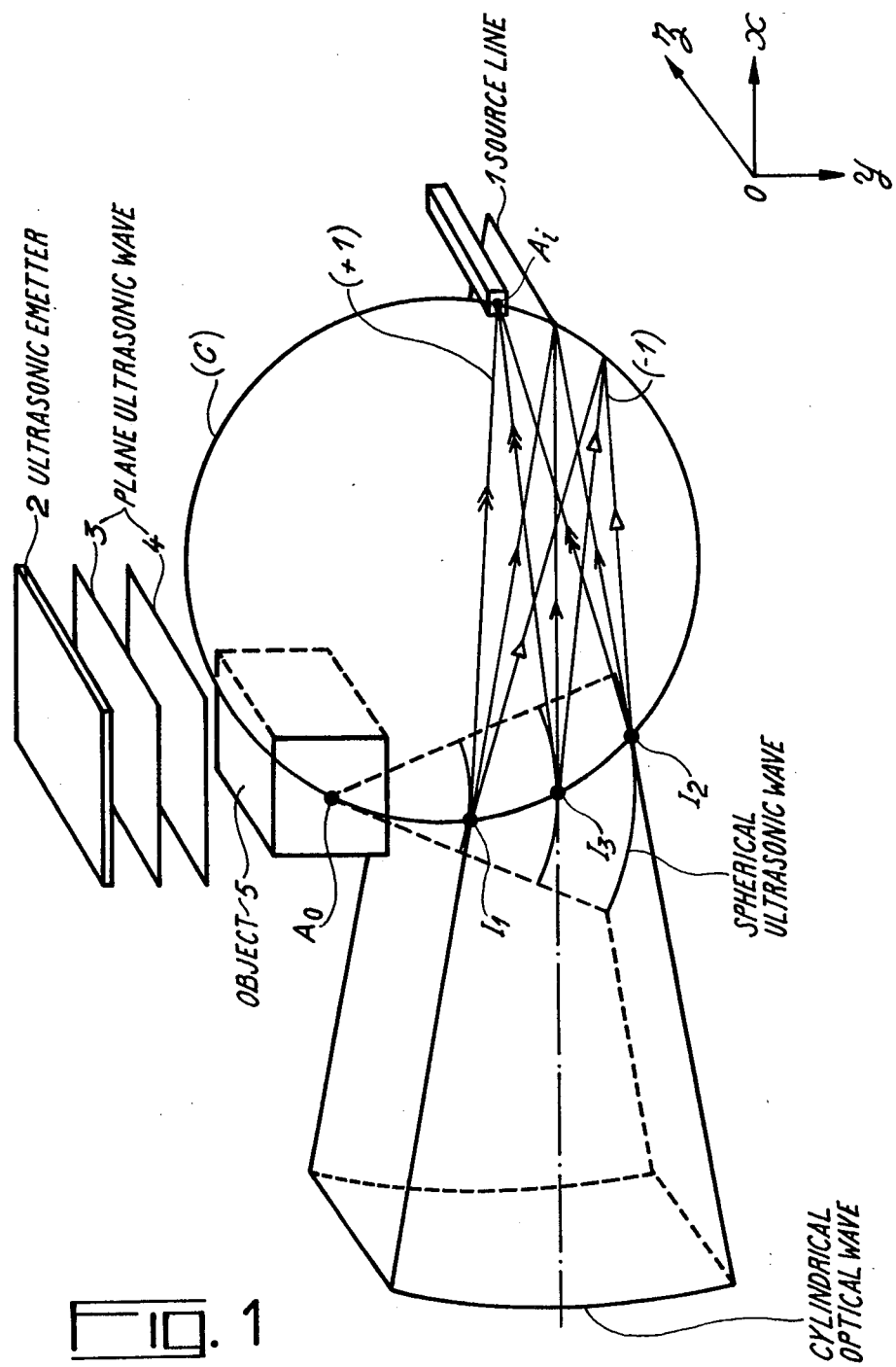
FIG. 1 is a diagram illustrating the phenomenon of acousto-optical interaction used in the imagery system according to the invention.

The acousto-optical imagery process hitherto adopted uses this angular selection effect. To this end, a field of cylindrical structure focussed on a source line 1 is produced as shown in FIG. 1. In addition, an ultrasonic plane wave is emitted by an emitter 2 (quartz or piezoelectric ceramic). This plane wave, represented by the planes 3 and 4, irradiates the object 5 to be analysed, this object being transparent to ultra sounds. Each point of the object, such as $A_O$, thus performs the function of an ultrasonic source point and emits a spherical wave having the same frequency as the incident ultrasonic wave. Assuming that the interaction phenomenon is limited to the interactions between the ultrasonic rays parallel to the principal sectional plane P, the plane P being a plane perpendicular to the optical source line 1, each optical ray acts as indicated above with the ultrasonic ray which forms with it an angle $(\pi/2) + \phi_B$, in which case the diffracted order $+1$ is obtained, and with the ultrasonic ray which forms with it the angle $(\pi/2) - \phi_B$, in which case the diffracted order $-1$ is obtained. The sound source point Ao, its optical image $A_i$, the interaction points $I_1, I_2, I_3 \ldots$ and the optical source point corresponding to the trace of the focal line 1 are situated on the same circle (C) belonging to a plane parallel to the plane P.

FIG. 1 shows the corresponding construction. An analogous construction for each of the points of the object makes it possible to show that a three-dimensional optical image of this object is formed. However, this image is not similar to the object being analysed. In the direction Oz of the focal line, the dimensions are maintained. By contrast, in the planes parallel to the principal sectional plane, the magnification is equal to the ratio $\lambda m/\lambda s$, i.e. if $\lambda m=0.5$ μm for example and $\lambda s=0.3$ mm, a magnification equal to 1/600. Accordingly, the optical image is greatly reduced in the directions Ox and Oy.

The anamorphosis thus produced may be corrected by means of an anamorphic optical device situated between the spatial filter filtering the desired diffraction order and the display unit so that the viewed image re-assumes the proportions which the object had. In conventional systems, the image is viewed through an image tube on the screen of a receiver after spatial filtering, and the quality of the images obtained is poor on account of the low resolution of the system which varies according to the directions and which depends upon the opening of the luminous beam in the direction Ox. In addition, in an imagery arrangement of this type, this resolution limit is further reduced by the aberrations introduced by the optical imagery system. In addition, the image obtained is disturbed by a significant noise level.

Figure 2:
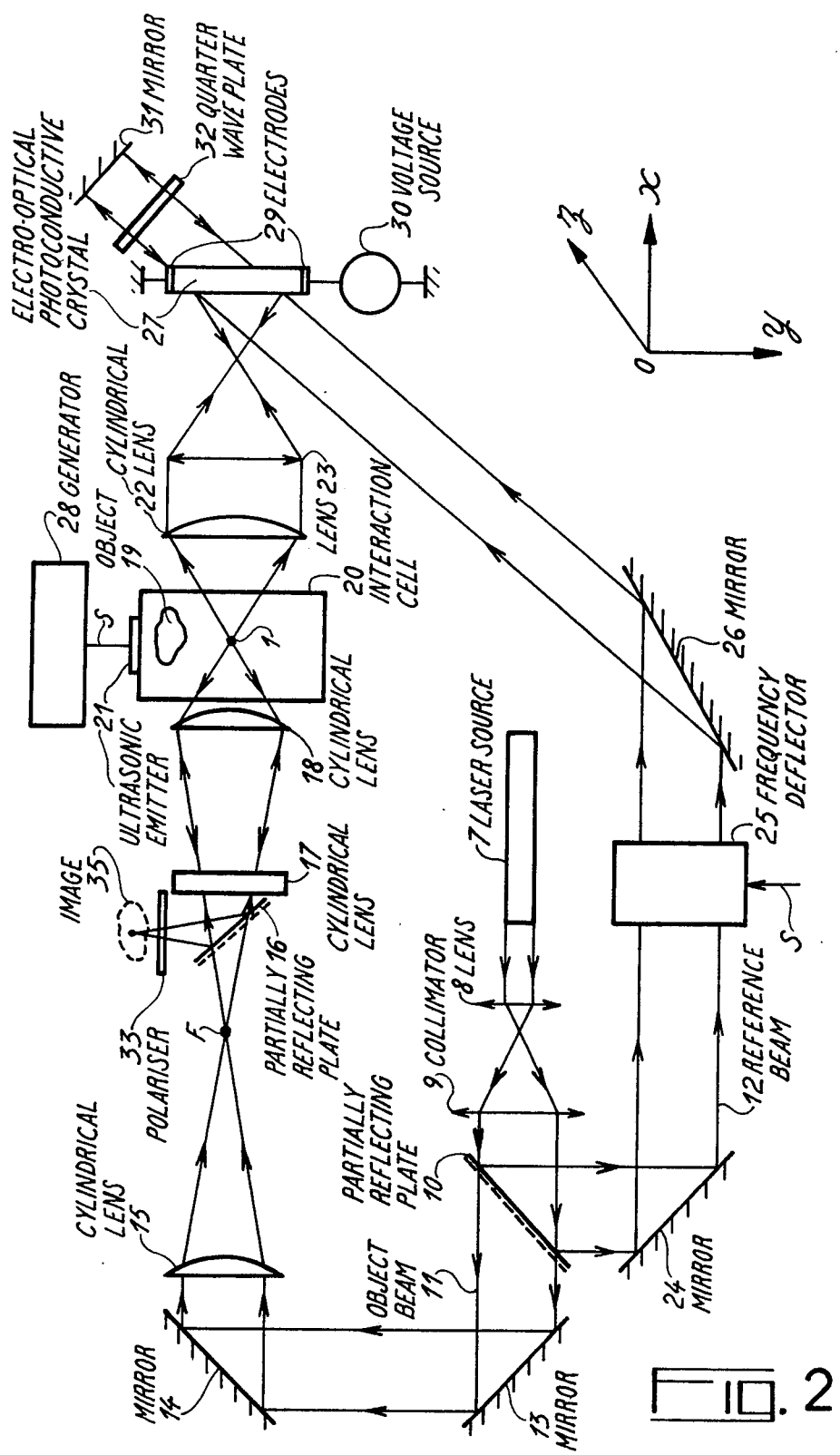
FIG. 2 is a diagram illustrating a first embodiment of the acousto-optical imagery system according to the invention.

FIG. 2 shows a plan of the acousto-optical imagery system according to the invention, this system enabling most of the above-mentioned disadvantages to be eliminated.

This system comprises a laser radiation source 7 of pulsation $\omega o$ and wave-length $\lambda o$ in air and $\lambda m$ in water. The laser source used, of the argon or helium-neon type, gives a monochromatic and coherent plane wave. This fine beam is focussed by a lens 8 and the beam emerging from the lens 8 is collimated by a collimator 9. The parallel beam thus formed is partially transmitted by a partially reflecting plate 10 to form an object beam 11 and partially reflected to form a reference beam 12, as will be explained hereinafter. An optical return system formed by the mirrors 13 and 14 directs the beam towards a cylindrical lens 15 which forms a focal line F of which the dimensions in the plane of the incident plane wave may be for example 100 μm in the direction Oy and 1 cm in the direction Oz, Ox being the axis of the optical beam. After having passed through the partially reflecting plate 16, the cylindrical optical wave is transmitted to a system of convergent cylindrical lenses consisting of a cylindrical lens 17 of which the generatrices are parallel to Oy and of a second cylindrical lens 18 of which the generatrices are parallel to Oz. The incident dihedron of laser light thus formed has a large opening. An interaction cell 20 containing water is traversed by this optical beam of pulsation $\omega o$. An ultrasonic emitter 21 is excited by a signal S emanating from a generator 28 emitting a signal at a frequency of from 1 to 15 MHz, the optimum frequency range being the range from 1 to 10 MHz. This ultrasonic emitter may be a quartz crystal or a piezoelectric ceramic. The object 19 to be analysed is placed in the cell in the path of the ultrasonic wave. The phenomenon of interaction between the ultrasonic wave and the cylindrical optical wave of pulsation $\omega o$ gives rise to a diffracted optical beam comprising in particular the diffracted optical beams of the first order of pulsation $(\omega_o+\omega_s)$ and $(\omega_o-\omega_s)$, $\omega_s$ being the pulsation of the sound wave. The beam emerging from the cell is intercepted by a cylindrical lens 22 to form a substantially plane wave, except for modulation, and the beam emerging from this lens 22 is collected by a collecting lens 23. The emerging beam consists of substantially flat waves. The optical reference beam 12 is directed by a return mirror 24 to a frequency deflector 25 which shifts the frequency of the reference beam so as to give it the same frequency as the diffracted optical wave to be detected to obtain an image of the object. If the diffracted order +1 is being detected, the corresponding pulsation of the detection beam is thus $\omega_o+\omega_s$. The deflector may be for example an acousto-optical deflector. The detection beam thus formed of pulsation $\omega_o+\omega_s$ controlled by the same generator 28 is directed by a return mirror 26 towards an electro-optical photoconductive crystal 27. Two electrodes 29 placed on lateral faces of this crystal are connected to a voltage source 30. An electrical field of high intensity, for example 6 KV/cm, is thus applied to the crystal. This crystal may be a crystal of $Bi_{12}SiO_{20}$ or $Bi_{12}GeO_{20}$ which have good optical qualities over a surface area of several square centimeters and a sensitivity under an applied field of the same order as that of high-resolution photographic plates. In addition, they can be recorded and erased indefinitely because their recording-erasing cycle is symmetrical. The energy per unit area required for erasure is equal to the energy used for recording, i.e. of the order of 0.1 mJ/cm$^2$ for the usual wave-lengths of a laser source of the argon type. The optical detection wave of pulsation $\omega_o+\omega_s$ forms with the diffracted optical wave of order +1 and the same pulsation a fixed network of interference fringes which evolves solely with the deformations of the object traversed by the ultrasounds. The interference network is holographically recorded in the crystal 27 in the form of a space charge field. The corresponding optical image may be restored in real time. To this end, a mirror 31 orthogonal to the optical axis of the detection beam and situated behind the crystal used for the coherent holographic detection reflects that fraction of the beam which is not used for the recording towards the crystal. This beam is used for reconstructing the object beam of the same pulsation $\omega_o+\omega_s$.

Since the hologram recorded in the crystal is three-dimensional, all the information contained in the ultrasonic object wave and then in the optical object beam has been recorded during the coherent holographic detection and the restored image is therefore a three-dimensional image.

The stationary waves between the reference wave and the reading wave which is the reference wave reflected by the mirror 31 are not recorded in the form of space charge variations, because the direction of the corresponding planes is substantially parallel to the direction of the applied field. Accordingly, the restored object wave corresponds solely to the diffracted order +1. This restored wave follows the inverse path of the object wave and therefore passes through the collecting lens 23, the cylindrical lens 22, the interaction cell and the system of cylindrical lenses 18 and 17 and is reflected by the partially reflecting plate 16. An image 35 of the object 19, which is stigmatic in every direction, is formed in the vicinity of the point conjugated with the trace of the focal line in relation to the partially reflecting plate 16. This image may be directly viewed on a screen capable of being moved along the optical axis of the beam for viewing different sections of the object.

If, in practice, the display unit did not comprise any other elements, a significant noise level would be superimposed upon the image obtained, this noise emanating from the ambient light. It is possible to separate the image from the noise because the recording crystal, which is both rotative and birefractive, modifies the polarisation of the beam which is applied to it. Since the cylindrical object wave and the reference wave are polarised rectilinearly, for example along the axis Oz, the reference wave emerging from the crystal and directed towards the mirror 31 has a slightly elliptical polarisation. A quarter-wave plate 32 for the optical reading wave is placed between the crystal and the mirror. By suitably orienting the neutral lines of this quarter-wave plate in relation to the axes of the ellipse, it can be shown that the restored optical object wave is of better quality and that its polarisation may be oriented substantially in the direction of the axis Ox.

A polariser 33 is thus placed orthogonally to the optical axis of the restored object beam just in front of the viewing plane. The image thus formed is of good quality and is substantially separated from the ambient optical noise.

With regard to the dimensions of the image in relation to the object, the various elements of the optical imagery system may be selected in such a way that the restored image has the same proportions as the object. Thus, if the object field is a surface measuring 3 cm $\times$ 3 cm the optical image obtained being reduced in the ratio $(\lambda m)/(\lambda s)$, i.e. 1/600, with the values $\lambda_m = 0.5$ $\mu$m and $\lambda_s = 0.3$ mm, the image field has become 50 $\mu$m $\times$ 50 $\mu$m in the plane (x,y). By contrast, in the direction Oz of the focal line, the magnification is equal to 1. The object of the optical system formed by the cylindrical lens 22 and the lens 23 is to form a substantially plane wave, as indicated above, which illuminates the entire surface of the crystal 27 used for the holographic detection so that, at the limits of the non-illuminated zones and in the direction of the applied field, the space charge field does not create an antagonistic field reducing the effect of the applied field. During restoration, the restored optical object wave forms after the lens 22 a restored optical image having the same dimensions as the direct optical image. The magnification of the lens 18 may be equal to 1 cm and the distance from the focal line F to this lens equal to 2 m. The magnification is thus of the order of 200 and the image obtained in the viewing plane thus measures 1 cm $\times$ 1 cm. If the magnification of the lens 17 in the direction of the focal line is selected equal to $\frac{1}{3}$, the third dimension is reduced to 1 cm for an initial length of 3 cm. Accordingly, the proportions of the three-dimensional optical image obtained are equal to the proportions of the viewed object.

Figure 3:
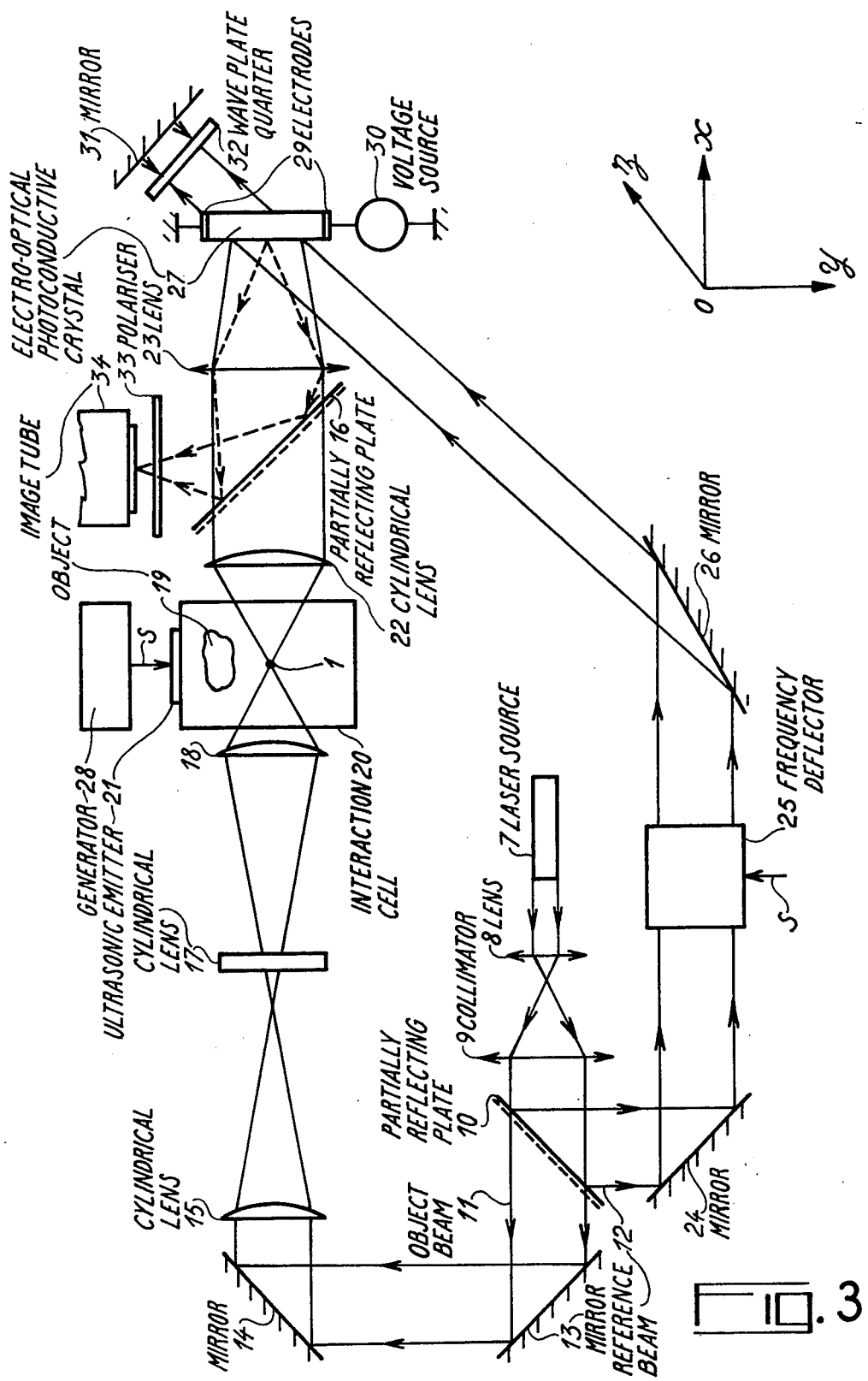
FIG. 3 is a diagram illustrating a second embodiment of the acousto-optical imagery system according to the invention.

FIG. 3 shows a second embodiment of the invention intended for viewing by a telescopic system. The same elements as in FIG. 2 have been denoted by the same references.

In FIG. 3, the optical path of the beam impinging on the crystal is exactly the same as that indicated in FIG. 2. By contrast, the path of the beam restored by the crystal is modified because the partially reflecting plate is no longer situated in the path of the object beam before passage through the cell, but instead in the path of the deflected object beam after the acousto-optical interaction with the ultrasonic wave having passed through the object. As indicated above, the viewed image is deformed in relation to the examined object, although an arrangement such as this can be useful for certain applications, for example applications in which only the qualitative data are to be viewed. The image is viewed by means of an image tube 34.

The invention is not limited to the embodiments of the acousto-optical imagery system based on coherent holographic detection which have been described and illustrated. In particular, the optical system intended to form the incident beam in the cell may be of any type provided that the wave formed is a convergent cylindrical wave, the opening of the beam being sufficient for the resolution obtained to be correct. Typically, the distance from the focal object trace line 1 to the centre of the lens 18 should amount to between f/2 and f, f being the focal length of this lens.

The numerical values given are only examples of the values capable of being used. Finally, the laser source used has been described as being an argon or helium-neon source because the holographic recording material used is sensitive to any radiation of which the wavelength is below or equal to that of radiation in the red region.

What we claim is:

1. An acousto-optical imagery system based on coherent holographic detection comprising an optical source of pulsation $\omega_o$, an electro-optical and photoconductive holographic recording crystal, a device forming a convergent cylindrical optical wave of pulsation $\omega_o$ from the wave emitted by the source, an ultrasonic cell containing a refractive fluid in which an object to be analysed is placed, an ultrasonic wave emitter emitting an ultrasonic wave of pulsation $\omega_s$, said ultrasonic wave passing through the object to be analyzed, said ultrasonic wave and said cylindrical optical wave interacting in the cell to form, by BRAGG diffraction of the optical wave, diffracted orders containing the optical images of said object to be analysed, an additional optical device intended to supply a plane optical reference wave of pulsation $\omega_o + k\omega_s$, k being equal to +1 or −1, according to whether the diffracted order to be imaged is the order +1 or −1, said diffracted order and said plane optical reference wave being directed towards said crystal to form interference fringes in said crystal; said electro-optical and photoconductive holographic recording crystal having electrodes connected to a voltage source, a unit for reconstructing from the interference fringes stored in said crystal an image of said object in real time; said unit comprising means for supplying from said source a plane optical reading wave having the same pulsation and direction as the reference wave, but being propagated in the opposite direction thereto, and an optical device forming said image of the object in a viewing plane from the read out beam reconstructed from said crystal, the object thus being viewed in real time.

2. An acousto-optical imagery system as claimed in claim 1, comprising a mirror orthogonal to the direction of propagation of the reference wave, said plane optical reading wave being formed by reflection of the optical reference wave passing through the recording crystal on said mirror.

3. An acousto-optical imagery system as claimed in claim 2, wherein a quarter wave plate for the reference wave is placed parallel to the mirror between the recording crystal and the mirror.

4. An acousto-optical imagery system as claimed in claim 1, wherein said image viewing unit is formed by the elements of said device forming said cylindrical optical wave, the beam restored by the recording crystal following an optical path opposite to that of the object wave impinging on the crystal, the magnification of this device being such that the proportions of the image formed are equal to the proportions of the object.

5. An acousto-optical imagery system as claimed in claim 1, wherein the recording crystal is a crystal of $Bi_{12}XO_{20}$, X being either silicon or germanium.

* * * * *